US006575924B2

(12) United States Patent
Wevers et al.

(10) Patent No.: US 6,575,924 B2
(45) Date of Patent: Jun. 10, 2003

(54) DEVICE FOR THE TREATMENT OF A REGION OF A HUMAN BODY, IN PARTICULAR FACIAL TREATMENT DEVICE

(75) Inventors: Dirk Hendrik Wevers, Drachten (NL); Arthur Putzer, Bad Eisenkappel (AT); Roland Stampf, Klagenfurt (AT); Bernd Kruschitz, Ludmannsdorf (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 92 days.

(21) Appl. No.: 09/902,220

(22) Filed: Jul. 10, 2001

(65) Prior Publication Data

US 2002/0049398 A1 Apr. 25, 2002

(30) Foreign Application Priority Data

Jul. 13, 2000 (EP) .............................................. 00890221

(51) Int. Cl.[7] ............................ A61H 7/00; A46B 13/02
(52) U.S. Cl. ............................ 601/112; 601/114; 15/28
(58) Field of Search ................................. 601/114, 112, 601/138, 137, 87, 17; 15/28, 180; 401/283, 287, 291

(56) References Cited

U.S. PATENT DOCUMENTS

| 4,454,867 A | * | 6/1984 | Swanson ...................... 601/114 |
| 5,187,827 A | * | 2/1993 | Wei ............................. 15/22.1 |
| 5,385,532 A | * | 1/1995 | Shyu ........................... 601/160 |
| 5,662,593 A | * | 9/1997 | Tillman et al. ............. 601/159 |
| 6,170,108 B1 | * | 1/2001 | Knight ......................... 15/29 |

FOREIGN PATENT DOCUMENTS

| DE | 8907950 | 8/1989 | ............ A46B/5/06 |
| DE | 9017453 | 4/1992 | ............ A61C/17/34 |
| EP | 0481553 A1 | 4/1992 | |
| FR | 935207 A | 6/1948 | |

* cited by examiner

Primary Examiner—Danton D. DeMille
(74) Attorney, Agent, or Firm—Ernestine C. Bartlett

(57) ABSTRACT

A device (1) for the treatment of a region of a body comprises the following components, i.e.: a housing (2) which can be held in one hand, a tool (10) provided for treating the region of the body, drive means (14) for driving the tool (10), and compression force definition means (65) for defining a desired compression force obtaining between the tool (10) and the region of a body under treatment, as well as adjustment means (66) accommodated in the housing (2) for adjusting the range for a desired compression force.

13 Claims, 1 Drawing Sheet

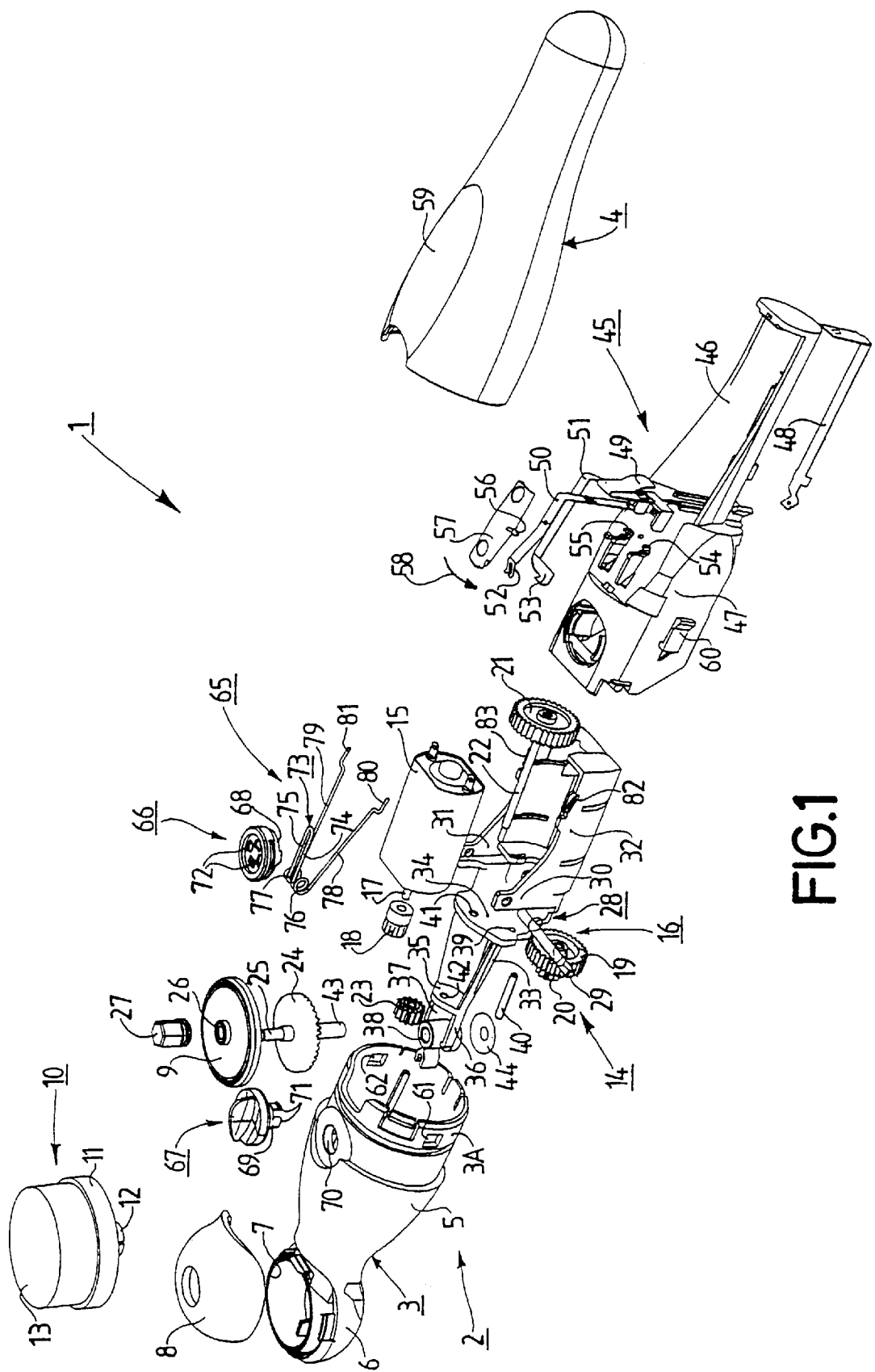

DEVICE FOR THE TREATMENT OF A REGION OF A HUMAN BODY, IN PARTICULAR FACIAL TREATMENT DEVICE

The invention relates to a device for the treatment of a region of a human body, which device comprises the following means: a housing which can be held by hand, a tool for treating a region of a body, drive means for driving said tool, and compression force definition means for defining a range for a desired compression force obtaining between the region of the body and the tool.

Such a device is known from the patent document EP 0 481 553 A1. This known device is an electric toothbrush with a brush head as the tool. In the known device, a blade spring of undulating shape is provided as the compression force definition means which is fastened by its one end to a non-adjustable support part connected to the housing of the known device and which accordingly engages this support part, and which by its other free end bears immediately on the drive means of the known device. The known device does indeed have a very simple constructional arrangement of its compression force definition means, but a desired compression force can only be defined within a given, and comparatively narrow range in this case by means of this simple constructional arrangement, which range is mainly defined by the spring characteristic of the blade spring provided.

The invention has for its object not only to enable a limited definition of a defined compression force in a device for the treatment of a region of a human body, but also to enable a comparatively multiple definition of a region for a desired compression force, and to provide an improved device in a simple manner by comparatively simple means.

To achieve the object indicated above, a device of the kind described in the opening paragraph according to the invention is characterized in that adjustment means are provided in the housing which are designed for adjusting the range for a desired compression force.

It is achieved by the measures according to the invention that several mutually different ranges for a desired compression force for pressing the tool of a device according to the invention against a body region under treatment can be set in a simple manner and by simple means, the adjustment of said ranges being achievable with said adjustment means with fine tuning. In spite of the achievable fine tuning, the solution is found by simple means.

Separate adjustment means may be provided in a device according to the invention. It was found to be very advantageous, however, if the adjustment means are formed by a support part which is adjustable relative to the housing by means of a manual control member. The support part, which is necessary anyway, is thus used at the same time as the adjustment means.

In connection with the above, it was found to be particularly advantageous if the adjustable support part comprises an adjustment cam which has a changing height gradient. A particularly fine tuning of the range for a desired compression force is achievable in this manner.

In connection with the above, it was found to be particularly advantageous if the adjustable support part is formed by a disc, and a rotary knob serving as the manual control member is connected to said disc, which knob has an extension which is passed through a hole in the housing and by means of which the rotary knob is connected to the disc. These embodiments were found to be advantageous as regards a comfortable adjustment of a desired compression force and as regards a simple mounting of the adjustable support part and the manual control member for rotating the compression force definition means.

In a device according to the invention, the compression force definition means may be realized by magnetic means or electromagnetic means. It was found to be particularly advantageous, however, if the compression force definition means are formed by spring means in a device according to the invention, as is known from the known device described in the preamble, in which the spring means are formed by a blade spring.

In a device according to the invention, the spring means may be realized not only through a blade spring configuration, but also through an alternative spring configuration. It was found to be particularly advantageous in the present case if the spring means are realized in the form of a wire spring.

It was found to be particularly advantageous in view of the above if the wire spring comprises a central portion bent into a U-shape and two spiraling spring portions as well as two load legs. This arrangement is characterized by a high simplicity and reliability. Furthermore, it is advantageous in this embodiment that the spiraling spring portions are utilized not only for their resilient action but also additionally for journaling the wire spring.

It was found to be very advantageous in a device according to the invention if the drive means are accommodated in retention means which are journaled about a pivot rod which is passed through the retention means, and if the retention means comprise two holder regions provided on either side of the pivot rod, of which regions one is designed for accommodating a motor and the other for accommodating part of a gear transmission. These embodiments were found to be particularly advantageous in practical tests, because a pivot point in the region of the center of gravity of the drive means can be easily achieved thereby.

Furthermore, it was found to be highly advantageous in relation to the use of a wire spring is this wire spring is journaled with its two spiraling spring portions on the pivot rod and if the wire spring bears with its two load legs on two spring leg receptacles of the retention means. These embodiments are advantageous for rendering mounting of such a wire spring as simple as possible.

It was found to be particularly advantageous when a device according to the invention is constructed as a facial treatment device. It should be noted, however, that a device according to the invention may alternatively be constructed as an electric toothbrush. It should further be noted that a device according to the invention need not only be constructed as a device for the treatment of a body region of a living creature, preferably of a human being, i.e. for the treatment of a region of a body consisting of organic substances, but that a device according to the invention may also be constructed for the treatment of a region of a body which is formed from inanimate components, for example from leather or metal or wood, in which case it would be a device for the treatment of shoes, or a device for the treatment of tableware or jewelry, or a device for the treatment of furniture.

The above and further aspects of the invention will become apparent from the embodiment described below and are further clarified with reference to this embodiment.

The invention will now be explained in more detail below with reference to an embodiment shown in the drawing, but the invention is by no means limited to this embodiment.

FIG. 1 shows a device representing an embodiment of the invention in exploded view.

In FIG. 1, a device 1 according to the invention is shown, which in this case is a facial treatment device which is constructed especially for cleaning and massaging the face of a human being. The device 1 comprises a housing 2 which can be held in one hand. The housing 2 consists of a front part 3 and a rear part 4. The front part 3 comprises a first front part portion 5 of tapering shape as seen in a direction away from the rear part 4 and a dish-shaped second front part portion 6 connected to the first front part portion 5 comprising an opening 7 which is covered by a cap part 8 of the housing 2. A membrane seal 9 is provided here between the second front part portion 6 and the cap part 8, by means of which seal a watertight construction of the housing 2 is safeguarded. The rear part 4 can be mounted to a connecting portion 3A of the front part 3, an O-ring seal (not shown) being provided in the region of the connecting portion 3A by means of which a watertight construction of the housing 2 is achieved.

The device 1 further comprises a tool 10 provided for the treatment of a human face, which tool is shown diagrammatically only in FIG. 1. The tool 10 under advisement is a facial treatment brush 10. The tool 10 comprises a substantially disc-shaped brush support 11 with a coupling sleeve 12 extending away therefrom in a direction towards the dish-shaped second front part portion 6. At the side facing away from the coupling sleeve 12, the brush support 11 carries a plurality of brushes 13 joined together into tufts, which tufts are indicated diagrammatically only in the form of a cylinder in FIG. 1.

The device 1 further comprises drive means 14 which are accommodated in the housing 2 and which are designed for driving the tool 10, for which purpose they are coupled to the tool 10. The drive means 14 comprise a motor 15 and a transmission 16. The motor 15 comprises a motor shaft 17 onto which a pinion 18 has been press-fitted. A first gear 19 of the transmission 16 is in engagement with the pinion 18. A second gear 20 is coaxially connected to the first gear 19 so as to be integral therewith. A third gear 21 of the transmission 16 is in engagement with the second gear 20. A first shaft 22 is fixedly connected to the third gear 21. A fourth gear 23 of the transmission 16 is press-fitted onto the first shaft 22 at the end of the first shaft 22 which faces away from the third gear 21. A crown gear 24 is in operational contact with the fourth gear 23. The crown gear 24 is fixedly connected to a second shaft 25 which is passed through an opening 26 in the membrane seal 9 and to whose free end a drive stud 27 of hexagonal cross-section is connected. The coupling sleeve 12 can be coupled to the drive stud 27, such that a locking connection obtains between the drive stud 27 and the coupling sleeve 12, which is not visible in FIG. 1. The tool 10 is coupled to the drive means 14 in this manner.

Retention means 28, which are pivotably journaled in the housing 2 about a pivot rod 29 passed through the retention means 28, are provided in the device 1 for the accommodation of the motor 15 and the transmission 16. For this purpose, the retention means 2 comprise journal side walls 30 and 31 each provided with a bore hole. The drive means 14 are adjustably supported with respect to the housing 2 by the retention means 28.

The retention means 28 comprise a first holder region 32 situated substantially at the side remote from the tool 10 with respect to the pivot rod 29, which region is substantially tub-shaped and is provided and constructed for accommodating the motor 15 of the drive means 14. The retention means 28 further comprise a second holder region 33 which is situated at the side facing the tool 10 with respect to the pivot rod 29 and which is substantially channel-shaped and comprises a first transverse wall 34 and a second transverse wall 35 as well as two channel wall extensions 36 and 37 between which a bearing sleeve 38 is accommodated.

In the region of the first transverse wall 34, a first bearing hole 39 is provided into which a bearing shaft 40 is pressed, onto which shaft the first gear 19 and the second gear 20 are supported so as to be rotatable. A second bearing hole 41 is furthermore provided in the first transverse wall 34, and a third bearing hole 42 is provided in the second transverse wall 35. The first shaft 22 is passed through the second bearing hole 41 and the third bearing hole 42 such that the first shaft 22 and the third gear 21 as well as the fourth gear 23 are rotatably supported by the retention means 28.

The bearing sleeve 38 serves to accommodate an end region 43 of the second shaft 25 in a rotatable manner, in which connection it should be noted that before the end region 43 is inserted into the bearing sleeve 38 an intermediate disc 44 is passed over the end region 43. The end region 43 of the second shaft 25 is locked against axial shifting with respect to the bearing sleeve 38 in a manner not shown in any detail.

A battery not shown in FIG. 1 is provided in the device 1 for supplying the motor 15 with electric power. To accommodate the battery, a battery holder 45 is provided in the housing 2 of the device 1, comprising a battery holder block and in addition also comprising a switch holder 47. Battery connection contacts 48 and 49 are connected to the battery holder 45. The battery connection contacts 48 and 49 are in electrical contact with two switch contacts 50 and 51 which are also provided at the battery holder 45 and whose free ends 52 and 53 can be brought into contact by means of a rocker switch 57, which is retained in a pivotable manner by two bearing supports 54 and 55 and two bearing studs 56, when the rocker switch 57 is pivoted in the direction of an arrow 58. The rocker switch 57 is present behind an elastically deformable cover portion 59 which was connected to the rear part 4 of the housing 2 by means of a two-component injection-molding process, by means of which cover portion 59 a user of the device 1 can operate the rocker switch 57 for switching the motor 15 on or off.

The switch holder 47 is comparable to a tunnel in shape, such that the first holder region 32 of the retention means 28 is accommodated in the holder space (not visible in FIG. 1) enclosed by the switch holder 47. It should be noted that the battery holder 45 is locked to the front part 3 of the housing 2 by means of two retaining hooks, of which only one retaining hook 60 is visible in FIG. 1, i.e. such that the two retaining hooks 60 grip into two openings 61 and 62 which are provided in the connecting portion 3A of the front part 3.

In addition, compression force definition means 25 are provided in the device 1 by means of which a range for a desired compression force can be adjusted, i.e. a compression force with which the tool 10, in this case the brushes 13 of the tool 10, can act on the face of a human being. The compression force definition means 65 comprise two regions bearing on the drive means 14 and one region bearing on a support part, which will be explained in more detail further below.

Furthermore, adjustment means 66 constructed for setting the range for a desired compression force are provided in the housing 2 of the device 1. The adjustment means 66 are formed here by a support part 66 which is adjustable with respect to the housing 2 by means of a manual control member 67. The adjustable support part 66 has an adjustment cam 68 which shows a gradient of changing height with respect to the region of the compression force definition means 65 bearing on the support part 66. The adjustment cam 68 has the shape of a circular arc in plan view, and the height gradient of the adjustment cam 68 corresponds to the principle of a sloping surface.

The adjustable support part 66 is formed by a rotatably supported disc 66 which is provided in the interior of the housing 2. A rotary knob 67 acting as the manual control member 67 is connected to the disc 66. The rotary knob 67 comprises an extension 69 which is passed through a hole 70 in the front part 3 of the housing 2. Four catches 71 extend in axial direction away from the extension 69 and are passed through four passages 72 in the disc 66 so as to grip behind the disc 66, so that the extension 69 and accordingly also the rotary knob 67 is connected to the disc 66, i.e. to the adjustment means 66, with a portion of the front part 3 of the housing 2 interposed therebetween.

The compression force definition means 65 are formed by spring means 65 in the device 61, which spring means 65 are realized in the form of a wire spring 65.

The wire spring 65 has a U-shaped bent central portion 73 with two spring legs 74 and 75 for cooperation with the adjustable support part 66. Furthermore, the wire spring 65 comprises two spiraling spring portions 76 and 77 each extending away from one of the two spring legs 74 and 75 and additionally provided for securing the wire spring 65 and keeping it in position. Furthermore, the wire spring 65 comprises load legs 78 and 79 each extending away from one of the two spiraling spring portions 76 and 77, which legs bear on the drive means 14, i.e. indirectly via the retention means 28. The wire spring 65 is journaled and kept in place with its two spiraling spring portions 76 and 77 on the pivot rod 29. The wire spring 65 grips with its load legs 78 and 79, i.e. with the angled ends 80 and 81 of the two load legs 78 and 79, into respective leg receptacles 82 and 83 provided at the first holder region 32 of the retention means 28.

In the device 1, the tool 10, i.e. the facial treatment brush 10, can be driven into rotation in only one direction of rotation by means of the motor 15 and the transmission 16. The rotary drive is possible here with only a single rotational speed in the device 1. Measures could be provided which enable a drive with several speeds. Furthermore, the drive of the facial cleaning brush could be designed so as to enable opposite directions of rotation in alternation.

When the rotatable support part 36 has been rotated into an end position by means of the manual control member 67, the result will be that the U-shaped bent central portion 73, which cooperates with the adjustment cam 68, is in an extreme position farthest away from the motor 15. In this case the wire spring 65 will have its lowest prestress. This lowest prestress of the wire spring 65 is chosen such that the retention means 28 loaded by the load legs 78 and 79 are held against a stop (not shown) in the housing 2 of the device 1. In this case, a comparatively small force exerted by a user's hand on the housing 2 of the device 1 will already have the effect that the tool 10 can be easily displaced over a certain total path length, which is limited by means of an end stop (also not shown) in the housing 2. As long as the user aims at keeping the tool within the total path length mentioned above, only a comparatively small compression force is exerted on the skin of the user's face under treatment in accordance with the small force exerted by the user.

When the adjustable support part 66 is rotated with the manual control member 67 such that the U-shaped bent central portion 73 of the wire spring 65 cooperating with the adjustable support part 66 is displaced from its extreme position in a direction towards the motor 15, the result will be that the prestress of the wire spring 65 is increased. This has the result that a stronger force is to be exerted on the housing 2 of the device 1 by a user of the device 1 if a displacement of the facial cleaning brush 10 within the total path length mentioned above is to be achieved, so that also a stronger compression force will be exerted on the region of the user's face under treatment by the facial cleaning brush 10. Accordingly, a suitable adjustment of the adjustable support part 66 realizes a prestress of the wire spring 65 of different value, which has the result that compression forces of different strengths can be applied to a region of a user's face under treatment by means of the facial cleaning brush 10, as long as the facial cleaning brush 10 is kept within the total path length mentioned above. Different operational conditions can thus be set in a simple manner, so that each user of the device 1 can choose a compression force experienced as pleasant and positive by him or her.

Means may additionally be provided which ensure that, for example, the power supply to the motor 15 is automatically cut or that the transmission between the motor 15 and the tool 10 is automatically interrupted in a situation in which the user of the device 1 exerts such a great force on the housing 2 of the device 1 that the tool 10 does not remain within the total path length mentioned above, i.e. the retention means 28 together with the drive means 14 perform an excessive pivoting movement inside the housing 2.

In the device 1 of FIG. 1, both the motor 15 and the gear transmission 16 of the drive means 14 are mounted to the retention means 28; i.e. the drive means are adjustable in their totality with the retention means 28, i.e. are pivotably mounted. This need not necessarily be the case; for example, the motor 15 may be held in a fixed position in the housing 2, while the transmission 16 is entirely or possibly partly connected to the retention means 28 and is accordingly adjustable, in which case the operational connection between the motor and a transmission part mounted to the retention means 28 must be of a flexible construction, for example as a flexible shaft.

What is claimed is:

1. A device (1) for the treatment of a region of a body, which device (1) comprises means as listed below, i.e.:
   a housing (2) which can be held in one hand, and
   a tool (10) provided for the treatment of the region of the body, and
   drive means (14) which are accommodated in the housing (2), which are adjustably supported with respect to the housing (2), which are constructed for driving the tool (10), and to which the tool (10) is coupled, and
   compression force definition means (65) by means of which a region for a desired compression force can be defined with which the tool (10) can act on the region of the body,
   and which comprise at least one region (78, 79) in engagement with the drive means (14) and
   at least one region (73) in engagement with a support part (66), and
   adjustment means (66) provided in the housing (2) and constructed for adjusting the range for a desired compression force.

2. A device (1) as claimed in claim 1, wherein the adjustment means (66) are formed by said support part (6) which is adjustable relative to the housing (2) by means of a manual control member (67).

3. A device (1) as claimed in claim 2, wherein the adjustable support part (66) comprises an adjustment cam (68) which has a changing height gradient with respect to the region (73) of the compression force definition means (65) bearing on the support part (66).

4. A device (1) as claimed in claim 3, wherein the adjustable support part (66) is formed by a rotatably supported disc (66) which is provided in the interior of the housing (2), and wherein a rotary knob (67) serving as the manual control member (67) is connected to said disc (66).

5. A device (1) as claimed in claim 4, wherein the rotary knob (67) has an extension (69) which is passed through a hole (70) in the housing (2) and which is connected to the disc (66).

6. A device (1) as claimed in claim 1, wherein the compression force definition means (65) are formed by spring means (65).

7. A device (1) as claimed in claim 6, wherein the spring means (65) are realized in the form of a wire spring (65).

8. A device (1) as claimed in claim 7, wherein the wire spring (65) comprises a central portion (73) bent into a U-shape with two spring legs (74, 75) for cooperation with the support part (66), and comprises two spiraling spring portions (76, 77) each extending away from one of the two spring legs (74, 75) and provided for journaling of the wire spring (65), and comprises two load legs (78, 79) which each extend from one of the two spiraling spring portions (76, 77) and which bear on the drive means (14).

9. A device (1) as claimed in claim 1, wherein the drive means (14) are accommodated in retention means (28) which are pivotably journaled about a pivot rod (29) passed through the retention means (28).

10. A device (1) as claimed in claim 3, wherein the retention means (28) comprise a first holder region (32) for the accommodation of a motor (15) of the drive means (14), which region lies substantially at the side remote from the tool (10) with respect to the pivot rod (29), and wherein the retention means (28) comprise a second holder region (33) for the accommodation of part of a transmission (16) provided between the motor (15) and the tool (10), which region lies at the side facing the tool (10) with respect to the pivot rod (29).

11. A device (1) as claimed in claim 8, wherein the wire spring (65) is journaled with its two spiraling spring portions (76, 77) on the pivot rod (29).

12. A device (1) as claimed in claim 11, wherein the wire spring (65) bears with its load legs (78, 79) on respective leg receptacles (82, 83) provided at the first holder region (32) of the retention means (28).

13. A device (1) as claimed in claim 1, wherein the device (1) is constructed as a facial treatment device (1) with a brush (10) which can be driven into rotation acting as the tool (10).

* * * * *